United States Patent [19]

Kawashima

[11] Patent Number: 4,796,604

[45] Date of Patent: Jan. 10, 1989

[54] ENDOSCOPE AND A LIGHT GUIDE THEREOF AND A METHOD FOR MANUFACTURING THE LIGHT GUIDE

[75] Inventor: Masahiro Kawashima, Hino, Japan

[73] Assignee: Olympus Optical Co., Ltd., Tokyo, Japan

[21] Appl. No.: 153,241

[22] Filed: Feb. 8, 1988

[30] Foreign Application Priority Data

Feb. 13, 1987 [JP] Japan ................................ 62-29732

[51] Int. Cl.$^4$ .............................................. A61B 1/06
[52] U.S. Cl. .................................... 128/6; 350/96.26
[58] Field of Search ......................... 128/3, 4, 5, 6, 7; 350/96.26

[56] References Cited

U.S. PATENT DOCUMENTS

| | | | |
|---|---|---|---|
| 2,975,785 | 3/1961 | Sheldon | 128/6 |
| 3,051,166 | 8/1962 | Hovnanian | 128/4 |
| 3,434,775 | 3/1969 | Gosselin | 128/6 X |
| 4,569,335 | 2/1986 | Tsuno | 128/6 |
| 4,576,147 | 3/1986 | Hashiguchi | 128/6 |
| 4,750,476 | 6/1988 | Forkner et al. | 128/6 |

FOREIGN PATENT DOCUMENTS

| | | |
|---|---|---|
| 51-61828 | 5/1976 | Japan . |
| 51-60853 | 5/1976 | Japan . |
| 53-10200 | 3/1978 | Japan . |
| 54-135537 | 9/1979 | Japan . |
| 58-190912 | 11/1983 | Japan . |

*Primary Examiner*—William H. Grieb
*Attorney, Agent, or Firm*—Ladas & Parry

[57] ABSTRACT

An endoscope comprises an insertion section and a light guide contained in the internal space of the insertion section and adapted to guide an illumination light. The light guide includes a number of elongated optical fibers having individual distal end portions, which are bound into bundle and bonded together. At least one spacing member is contained in the distal end portion of the bundle of optical fibers, with the optical fibers kept loose on the proximal-end side of the distal end portion of the optical fiber bundle to provide gaps among the optical fibers.

12 Claims, 2 Drawing Sheets

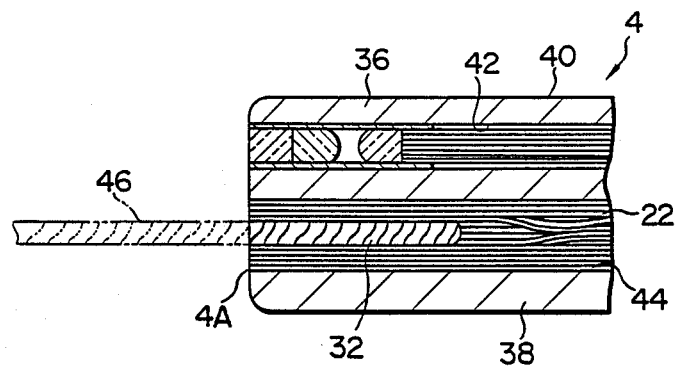
FIG. 4
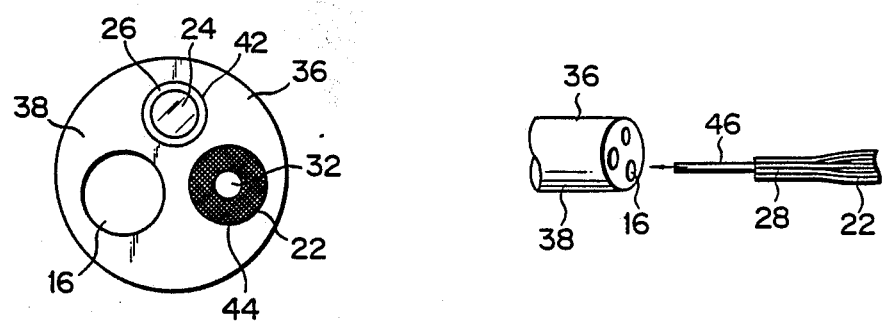
FIG. 5
FIG. 6

ENDOSCOPE AND A LIGHT GUIDE THEREOF AND A METHOD FOR MANUFACTURING THE LIGHT GUIDE

BACKGROUND OF THE INVENTION

1. Field of the Invention

The present invention relates to an endoscope with a light guide composed of a bundle of optical fibers and a method for manufacturing the light guide.

2. Description of the related art including information disclosed under § 1.97-1.99:

In conventional endoscopes, an illumination light is supplied to the distal end of an insertion section through a bundle of optical fibers. The fiber bundle includes a number of elongate glass fibers o optical fibers. These fibers are bundled and contained inside the insertion section. The distal end portion of the optical fiber bundle is solidified by means of a bonding agent or the like, and is fitted with a mouthpiece thereon. The mouthpiece is attached to the distal end portion of the insertion section of the endoscope. The distal end portion of the fiber bundle is solidified as follows. First, those parts of the glass fibers at the distal end portion ar bundle closely and inserted into a die. Then, the bonding agent is poured into the die. At the proximal end portion of the optical fiber bundle, on the other hand, the individual glass fibers are kept free, without being bundled, in order to maintain flexibility.

If the proximal end portion of the optical fiber bundle, as well as the distal end portion, is joined close to one another when it is contained in the insertion section, its free action is restrained. As a result, the fiber bundle, and therefore, the insertion section of the endoscope, lose their flexibility.

Thereupon, in a typical endoscope, such as the one disclosed in Japanese Patent Disclosure No. 58-190912, the side wall of a cylindrical mouthpiece, used to retain the distal end portion of an optical fiber bundle, is thickened. Also, a sufficient space is secured between the outer peripheral surface of the fiber bundle and the inner peripheral surface of a holding portion of an insertion section of the endoscope. Thus, the density of glass fibers is lowered at the proximal end portion of the fiber bundle.

In such a typical endoscope, the side wall of the mouthpiece at the distal end portion of the insertion section is thick, as described above, so that the insertion section must have a large outside diameter. Thus, the insertion section is too bulky and heavy.

SUMMARY OF THE INVENTION

The object of the present invention is to provide an endoscope in which the side wall of a mouthpiece for retaining a bundle of optical fibers is made relatively thin so that an insertion section has a relatively small outside diameter and is light in weight.

The above object of the present invention is achieved by an endoscope constructed as follows. The endoscope comprises an insertion section and a light guide contained in the internal space of the insertion section and adapted to guide an illumination light. The light guide includes a number of elongate optical fibers individually having distal end portions, which are bound into a bundle and bonded together. At least one spacing member is contained in the distal end portion of the bundle of optical fibers, with the optical fibers kept loose on the proximal-end side of the distal end portion of the optical fiber bundle to provide gaps among the optical fibers.

In the endoscope of the invention, the spacer is contained in the distal end portion of the optical fiber bundle, and only those parts of the optical fibers at the distal end portion ar joined closely and bonded together. Thus, the density of the optical fibers on the proximal-end side of the distal end portion is lowered, so that the flexibility of the fiber bundle can be maintained. Moreover, the density of the proximal end portion of the optical fiber bundle can be easily changed by only changing the thickness of the spacer. Furthermore, the side wall of a mouthpiece, which is fitted on the distal end portion of the fiber bundle, can be made relatively thin.

BRIEF DESCRIPTION OF THE DRAWINGS

FIG. 4 is a longitudinal sectional view showing an insertion section of an endoscope according to a second embodiment of the invention;

FIG. 5 is a front view of the insertion section shown in FIG. 4; and

FIG. 6 is a perspective view showing a method for manufacturing a light guide of the endoscope according to the present invention.

DETAILED DESCRIPTION OF THE PREFERRED EMBODIMENTS

Preferred embodiments of the present invention will now be described in detail with reference to the accompanying drawings.

Figure 1:
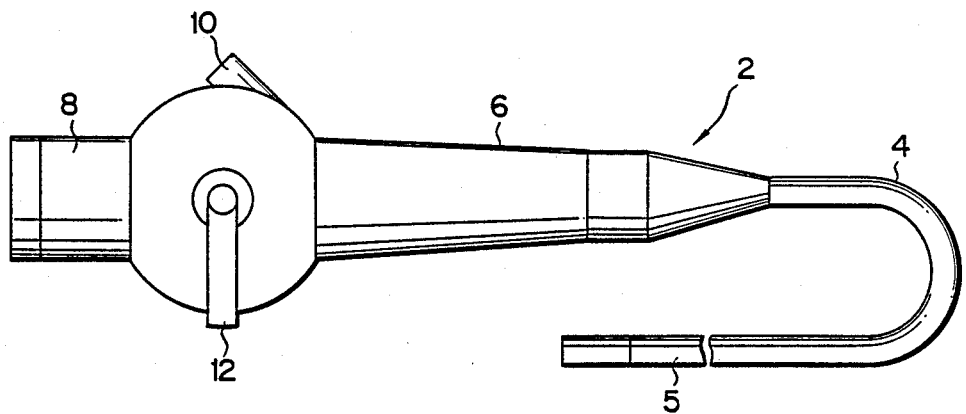
FIG. 1 is a side view showing an outline of an endoscope according to the present invention.
Figure 2:
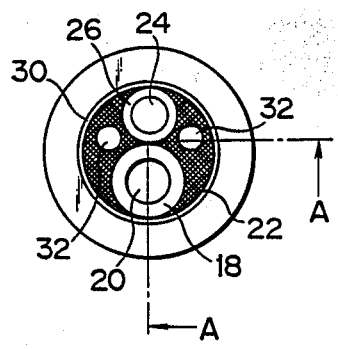
FIG. 2 is a front view showing an insertion section of an endoscope according to a first embodiment of the present invention.
Figure 3:
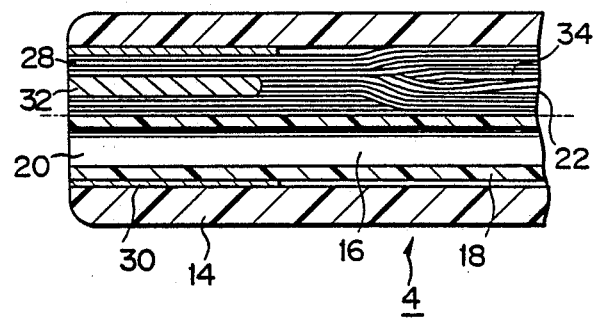
FIG. 3 is a sectional view taken along line A—A of FIG. 2.

FIGS. 1 to 3 show a first embodiment of the endoscope of the present invention. As shown in FIG. 1, endoscope 2 comprises insertion section 4, having a relatively small outside diameter, and control section 6 for controlling the endoscope. An universal cord (not shown) is connected to section 6. Control section 6 includes eyepiece portion 8, inlet port 10 through which an medical instrument or the like is inserted into the endoscope, and bending control lever 12 for operating a bending portion 5 at the distal end portion of insertion section 4.

As shown in FIGS. 2 and 3, insertion section 4 includes flexible sheathing tube 14, in which channel 16 for the medical instrument or the like is arranged. Channel 16, which is formed of flexible tube 18, opens into inlet port 10 of control section 6 and opening 20 at the distal end of insertion section 4. Section 4 contains therein optical fiber bundle 22, used to supply illumination light, and another optical fiber bundle used (not shown) for observation. The distal end of the observation fiber bundle is situated on the same axis as objective lens 24, which is disposed inside the distal end portion of insertion section 4. Lens 24 is held in position by means of cylindrical lens frame 26. Further, the observation fiber bundle extends from the distal end of insertion section 4 to eyepiece portion 8 of control section 6, and its proximal end portion is situated on the same axis as eyepiece of portion 8.

As shown in FIGS. 2 and 3 the respective distal end portions of flexible tube 18, lens frame 26 surrounding the optical fiber bundle for observation, and optical fiber bundle 22 used for illumination are contained within cylindrical retaining frame 30. Frame 30 is in close contact with the inner surface of sheathing tube 14, and is bonded thereto by means of a bonding agent so as to be water and airtight. The spaces between the inner peripheral surface of retaining frame 30 and the respective outer peripheral surfaces of tube 18 and lens frame 26 are tightly packed with a number of optical fibers, which constitute the illumination fiber bundle 22. Moreover, at the distal end portion 28 of fiber bundle 22, the spaces between the individual optical fibers are filled with a bonding agent so that the fibers adhere to one another.

In the light guide of the endoscope according to the present invention, furthermore, rod-shaped spacers 32, each having a circular cross section, are fitted in distal end portion 28 of optical fiber bundle 22. In this first embodiment, two spacers 32 are prepared in advance, and are inserted between the optical fibers before the bonding agent solidifies end portion 28. Then, each spacer is bonded together with the respective distal end portions of the optical fibers.

Thus, inside the internal space of the cylindrical retaining frame 30 having a predetermined inside diameter, distal end portion 28 of optical fiber bundle 22 used for illumination is constructed s that the spaces between the individual optical fibers are reduced, that is, the fibers are fixed so as to be closer to one another. In this embodiment, that part of distal end portion 28 solidified by means of the bonding agent has a length ranging, for example, from several millimeters to tens of millimeters, extending from the distal end portion insertion section 4. At flexible portion 34 on the proximal-end side of solidified distal end portion 28, the individual optical fibers are left unbound and flexible. A lubricant or the like is sealed in flexible portion 34, whereby damaged due to friction of the fibers rubbing against on another is prevented.

In the light guide of the endoscope according to the present invention, as described above, spacers 32 are placed in distal end portion 28 of optical fiber bundle 22. Accordingly, the optical fibers are packed tightly in the internal space of cylindrical retaining space 30 which has a predetermined inside diameter. The outside diameter of fiber bundle 22 increases since spacers 32, as well as channel tube 18 and lens frame 26, are located in distal end portion 28 of the fiber bundle. Within flexible portion 34 of fiber bundle 22, spacers 32 are not present so the gaps between the individual optical fibers are thereby extended, increasing the degree of fiber flexibility.

In the light guide of the endoscope according to the present invention, moreover, the cross section of each spacer 32 is not limited to the truly circular configuration, and may alternatively be oval in shape, for example. As shown in FIG. 3, however, each spacer 32 must be shorter than solidified distal end portion 28.

FIGS. 4, 5 and 6 show an endoscope according to a second embodiment of the present invention. In this second embodiment, multi-lumen tube 38 is used as sheathing tube 36 of insertion section 4. The individual lumens of tube 38 are used as channel 42 containing optical fiber bundle 40 used for observation or image transfer, channel 16 for conducting forceps or the like, and channel 44 containing optical fiber bundle 22 for illumination.

Spacer 32, which constitutes part of wire 46, is inserted in the distal end portion of illumination fiber bundle 22, and is solidified by means of a bonding agent or the like, as in the case of the first embodiment. Thus, by means of spacer 32, the optical fibers are more closely joined at distal end portion 28 than at the flexible portion on the proximal-end side. More specifically, fiber bundle 22 which has a fixed outside diameter does not contain spacer 32 within its proximal end portion. Therefore, the gaps between the individual optical fibers at the proximal end portion are extended, so that the fibers are more flexible.

A method of inserting illumination fiber bundle 22 and spacer 32 into channel 44 of the insertion section of the endoscope will now be described.

As shown in FIG. 6, one end portion of wire 46, which serves as spacer 32, is inserted into distal end portion 28 of optical fiber bundle 22. Then, these end portions are externally clamped to be bonded together. Subsequently, the other end portion of wire 46, having the one end portion connected to distal end portion 28 of fiber bundle 22, is inserted into channel 44 of sheathing tube 36 through the opening of control section 6 of the endoscope, and is drawn out through the distal-end opening of channel 44. Fiber bundle 22 is drawn into channel 44 by further drawing out wire 46. When distal end portion 28 reaches the distal-end opening portion of channel 44, as shown in FIG. 4, it is fixedly bonded to the inner peripheral surface of the distal-end opening portion in a watertight manner. Thereafter, that portion of wire 46 projecting from distal end face 4A of insertion section 4 is cut off.

In the second embodiment, one integral wire serves both as spacer 32 and wire 46 adapted for the insertion of optical fiber bundle 22 into channel 44. Thus, the light guide of the endoscope ca be assembled with ease.

It is to be understood that the present invention is not limited to the embodiments described above, and may be also applied, for example, to a rigid endoscope in which the sheath of the insertion section of the first embodiment is formed of a rigid member.

What is claimed is:

1. An endoscope comprising:
    an insertion section having an internal space;
    light guide means contained in the internal space of the insertion section and adapted to guide a illumination light, said light guide means including a number of elongated optical fibers having individual distal end portions bound into a bundle and bonded together; and
    spacing means contained in the distal end portion of the bundle of optical fibers, with the optical fibers kept loose on the proximal-end side of the distal end portion of the optical fiber bundle to provide gaps among the optical fibers.

2. The endoscope according to claim 1, wherein said spacing means includes a spacer for securing a predetermined space within the distal end portion of the optical fiber bundle.

3. The endoscope according to claim 2, wherein said spacer is formed of a rod-shaped member which has a circular cross section and is shorter than the bonded distal end portion of the optical fiber bundle.

4. The endoscope according to claim 2, wherein said spacer is formed of a rod-shaped member which has an oval cross section and is shorter than the bonded distal end portion of the optical fiber bundle.

5. The endoscope according to claim 1, wherein said insertion section includes a multi-lumen tube, said light guide means being contained in one of the lumens of said tube.

6. A light guide of an endoscope, comprising:
a number of elongated optical fibers for guiding an illumination light, the respective distal end portions of said optical fibers being tightly bound into a bundle and bonded together; and
spacing means contained in the distal end portion of the optical fiber bundle, with the optical fibers of the optical fiber bundle kept loose on the proximal-end side of the distal end portion to provide gaps among the optical fibers.

7. The light guide according to claim 6, wherein said spacing means includes a spacer for securing a predetermined space within the distal end portion of the optical fiber bundle.

8. The light guide according to claim 7, wherein said spacer is formed of a rod-shaped member which has a circular cross section and is shorter than the bonded distal end portion of the optical fiber bundle.

9. The light guide according to claim 7, wherein said spacer is formed of a rod-shaped member which has an oval cross section and is shorter than the bonded distal end portion of the optical fiber bundle.

10. A method for manufacturing a light guide of an endoscope, comprising the steps of:
binding a plurality of optical fibers into a bundle;
inserting spacing means into the distal end portion of the bundle of optical fibers, with the optical fibers kept loose on the proximal-end side of the distal end portion of the optical fiber bundle to provide gaps among the optical fibers.

11. The method according to claim 10, wherein said spacing means includes a spacer for securing a predetermined space within the distal end portion of the optical fiber bundle.

12. The method according to claim 11, further comprising the steps of:
previously fixing one end portion of a wire, for use as the spacer, in the distal end portion of the optical fiber bundle;
inserting the other end portion of the wire into the internal space of an endoscope insertion section;
introducing the optical fiber bundle into the internal space while simultaneously pulling the other end portion of the wire;
fixing the distal end portion of the optical fiber bundle to a distal-end opening portion of the internal space; and
cutting off that portion of the wire which projects from the distal-end opening portion.

* * * * *